US009832996B2

(12) United States Patent
Boddy et al.

(10) Patent No.: US 9,832,996 B2
(45) Date of Patent: Dec. 5, 2017

(54) USE OF SARMENTINE AND ITS ANALOGUES WITH AN HERBICIDE, AND COMPOSITIONS THEREOF

(71) Applicant: Marrone Bio Innovations, Inc., Davis, CA (US)

(72) Inventors: Louis Boddy, Davis, CA (US); Pamela Marrone, Davis, CA (US); Matthew Robinson, Davis, CA (US)

(73) Assignee: Marrone Bio Innovations, Inc., Davis, CA (US)

( * ) Notice: Subject to any disclaimer, the term of this patent is extended or adjusted under 35 U.S.C. 154(b) by 0 days.

(21) Appl. No.: 15/026,279

(22) PCT Filed: Sep. 17, 2014

(86) PCT No.: PCT/US2014/056054
§ 371 (c)(1),
(2) Date: Mar. 31, 2016

(87) PCT Pub. No.: WO2015/050705
PCT Pub. Date: Apr. 9, 2015

(65) Prior Publication Data
US 2016/0212999 A1 Jul. 28, 2016
US 2017/0196222 A9 Jul. 13, 2017

Related U.S. Application Data

(60) Provisional application No. 61/885,449, filed on Oct. 1, 2013.

(51) Int. Cl.
*A01N 43/653* (2006.01)
*A01N 43/36* (2006.01)

(52) U.S. Cl.
CPC ........... *A01N 43/653* (2013.01); *A01N 43/36* (2013.01)

(58) Field of Classification Search
CPC .............................. A01N 43/653; A01N 43/36
See application file for complete search history.

(56) References Cited

U.S. PATENT DOCUMENTS

| | | | |
|---|---|---|---|
| 4,453,975 A | 6/1984 | Takematsu et al. |
| 5,665,681 A | 9/1997 | Seckinger et al. |
| 6,821,926 B1 | 11/2004 | Feucht et al. |
| 6,825,216 B1 | 11/2004 | Trail et al. |
| 2007/0142228 A1 | 6/2007 | Haas |
| 2008/0242740 A1 | 10/2008 | Ley et al. |
| 2008/0317923 A1 | 12/2008 | Ley et al. |
| 2009/0124701 A1 | 5/2009 | Langer et al. |
| 2010/0323894 A1 | 12/2010 | Hacker et al. |
| 2011/0021358 A1 | 1/2011 | Huang et al. |

FOREIGN PATENT DOCUMENTS

| | | |
|---|---|---|
| DE | 225325 A | 7/1985 |
| JP | 408268954 A | 10/1996 |
| WO | 2007104669 A2 | 9/2007 |
| WO | 2008065451 A2 | 6/2008 |
| WO | 2008135093 A1 | 11/2008 |
| WO | WO 2014139870 A1 * | 9/2014 ............ A01N 25/14 |

OTHER PUBLICATIONS

Amicarbazone WDG Herbicide Label Amendment, Jul. 2012, United States Evironmental Protection Agency, Office of Chemical Safety and Pollution Prevention, pp. 1-22.*
Abarbri et al., "A Synthetic Approach to Natural Dienamides of Insecticidal Interest". Synthetic Communications. 1998, vol. 28, No. 2, pp. 239-249.
Alexander, J.P., et al., "The putative endocannabinoid transport blocker LY2183240 is a potent inhibitor of FAAH and several other brain serine hydrolases." J. Am. Chem. Soc. Apr. 29, 2006, vol. 128, pp. 9699-9704.
Askolar, R., et al., "Daramides A-C, Weakly cytotoxic polyketides form a marine-derived actinomycete of the genus *Streptomyces* strain CNQ-085." J. Nat Prod. Aug. 3, 2006, vol. 69, pp. 1756-1759.
Batish, D. R., et al., "Phytotoxicity of lemon-scented eucalypt oil and its potential use as a bioherbicide." Crop Protection 23, May 9, 2004, pp. 1209-1214.
Bednarek et al., "Novel Polymers Based on Atom Transfer Radical Polymerization of 2 Methoxyethyl Acrylate". Journal of Polymer Science. 2007, vol. 45. pp. 333-340.
Bemabeu, M., et al., "(2E,4E)-5-Tosyl-2,4-pentadienamides: New dienic sulfones for the stereoselective synthesis of (2E,4E)-dienamides." Tetrahedron Letters vol. 36, No. 22, 1995. pp. 3901-3904.
Bertin, C., "Grass roots chemistry: meta-tyrosine, an herbicidal nonprotein amino acid." Proc. Nat'l. Acad. Sci. USA vol. 104, No. 43 16964-16969. Oct. 23, 2007.
Carter, P., et al., "Probing the mechanism and improving the rate of substrate-assisted catalysis in subtilisin BPN." Biochem. 30, 6142-6148. Apr. 1991.
Cho, J., et al., "Lucentamycins A-D, cytotoxic peptides from the marine-derived actinomycete nocardiopsis lucentensis." J. Nat Prod. vol. 70, No. 8, 1321-1328. Mar. 7, 2007.
Choi, E.M., et al., "Investigations of anti-inflammatory and antinociceptive activities of Piper cubeba, Physalis angulata and Rosa hybrid." J. Ethanopharmacol. 89, 171-175. Jul. 25, 2003.
Corey, D. R. and Craik, C. S. "An investigation into the minimum requirements for peptide hydrolysis by mutation of the catalytic triad of trypsin," J. Am. Chem. Soc. vol. 114, No. 5, 1784-1790. 1992.

(Continued)

*Primary Examiner* — Mina Haghighatian
*Assistant Examiner* — Andriae M Holt
(74) *Attorney, Agent, or Firm* — Chainey P. Singleton

(57) ABSTRACT

Disclosed herein are methods for modulating (e.g., inhibiting) emergence and growth of monocotyledonous or dicotyledonous plants (e.g., weeds and grasses) using sarmentine and/or a sarmentine analog and a second herbicide. The application of sarmentine and/or a sarmentine analog with a second herbicide to a plant and/or its growth substrate results in a synergistic pre- and/or post-emergence herbicidal activity against the plant. The present method also provides compositions comprising sarmentine and/or a sarmentine analog, in combination with a second herbicide.

3 Claims, No Drawings

(56) References Cited

OTHER PUBLICATIONS

Cornacchione, S., "In vivo skin antioxidant effect of a new combination based on a specific *Vitis vinifera* shoot extract and a biotechnological extract" J. Drugs in Dermatol. 6S, 8-13. 2007.
Das, Biswanath., et al., "Aikamides and other constituents of Piper longum." PlantaMed 62, 582. May 4, 1996.
Database CA [Online] Chemical Abstracts Service, Columbus, Ohio, US; XP002687722, retrieved from STN Database accession No. 1981:514761.
Duke, S. 0., et al., "Chemicals from nature for weed management" Weed Sci. 50, 138-151. Mar.-Apr. 2002.
Examination Report for NZ App. No: 598271 dated Oct. 18, 2012.
Extended Search Report for EP. App. No. 10802779.8 dated May 12, 2012.
Fukuda, M., et al., "Phytotoxic activity of middle-chain fatty acids I: effects on cell constituents" Pest Biochem. Physiol., 80, 143-150. Jun. 25, 2004.
Ghoshal, S.,et al., "Antiamoebic activity of *Piper longum* fruits against Entamoeba histolytica in vitro and in vivo" J. Ethanopharmacol. 50, 167-170. Jan. 8, 1996.
Gianessi, L P. and Reigner, N. P. "The value of herbicides in U.S. crop production." Weed Technol 21, 559-566. Apr.-Jun. 2007.
International Search Report and Written Opinion for PCT/US2010/042607, dated Feb. 23, 2011.
Kiuchi et al., "Studies on Crude Drugs Effective on Visceral Larva Migrans. IV. Isolation and Identification of Larvicidal Principles in Pepper". Chern. Pharm. Bull. 1988, vol. 36, No. 7 pp. 2452-2465.
Krishnamurthi, A The Wealth of India Raw Materials, vol. 8. CSIR, New Delhi, India, p. 96. 1969.
Lederer, B., et al., "Phytotoxic activity of middle-chain fatty acids II: peroxidation and membrane effects" Pest Biochem. Physiol. 80. 151-156. Jun. 25, 2004.
Li, Cy., et al., "Isolation and identification of antiplatelet aggregatory principles from the leaves of Piper lolot" J. Agric. Food Chem. 55, 9436-9442. 2007.
Likhitwitayawuid, K., et al., "Structural Elucidation and Synthesis of New Components isolated from Piper Samentosum" Tetrahedron vol. 43, No. 16, 3689-3694. Jun. 2, 1987.
Macias, F. A., et sl., "Allelopathy—a natural alternative for weed control." Pest Manag Sci., 63, 327-348. 2007.
Mata, R., et al., "Antimycobacterial compounds from Piper sanctum" J. Nat. Prod. vol. 67, No. 12, 1961-1968. Dec. 2004.
Nalina et al., "The Crude Aqueous Extract of *Piper belle* L. and its Antibacterial Effect Towards *Streptococcus mutans*". American Journal of Biotechnology and Biochemistry. 2007, vol. 3, No. 1, pp. 10-15.
Parma, V., et al., "Phytochemistry of the Genus *Piper*" Phytochem. vol. 46, No. 4, 597-673. 1997.
Parma, V., et al., "Polyphenols and Alkaloids from *Piper* Species." Phytochem. vol. 49, No. 4 1069-1078. Mar. 2, 1998.
Rukachaisirikul, T., et al., "Chemical constituents and bioactivity of Piper sarmentosum" J. Ethnopharmacol. 93, 173-176. Jan. 30, 2004.
Siddiqui et al., "New Insecticidal Amides from Petroleum Ether Extract of Dried *Piper nigrum* L. Whole Fruits." Chemical Pharm. Bull. vol. 52, No. 11, 1349-1352, Nov. 2004.
Solomon, G. M. and Schettler, T. "Environment and health: 6. Endocrine disruption and potential human health implications" Can Med Assoc J vol. 163, No. 11, 1471-1476. Nov. 28, 2000.
Stillerman, K. P., et al., "Environmental exposures and adverse pregnancy outcomes: A review of the science" Reproductive Sci. vol. 15, No. 7, 631-650. Sep. 2008.
Tuntiwachwuttikul, P., et al., "Chemical constituents of the roots of Piper Sarmentosum" Chem. Pharm. Bull. vol. 54, No. 2, 149-151. Feb. 2006.
Vedhanayaki, G., et al., "Analgesic activity of *Piper longum* Linn. Root" Ind. J. Exp. Bioi. 41,649-651, Jun. 2003.
Whaley, C. M., et al., "A new mutation in plant ALS confers resistance to five classes of ALS- inhibiting herbicides," Weed Sci. 55, 83-90. Mar.-Apr. 2007.
Yang, Y. C., et al., "A piperidine amide extracted from *Piper longum* L fruit shows activity against *Aedes aegypti* Mosquito Larvae" J. Agric. Food Chem. 50, 3765-3767. May 18, 2002.

\* cited by examiner

USE OF SARMENTINE AND ITS ANALOGUES WITH AN HERBICIDE, AND COMPOSITIONS THEREOF

CROSS REFERENCE TO RELATED APPLICATIONS

This application claims priority to, and is the National Phase of International Application No. PCT/US2014/056054, filed on Sep. 17, 2014, which claims the benefit under 35 U.S.C. §119(e) of U.S. Provisional Application No. 61/885,449, filed Oct. 1, 2013. All of which are hereby incorporated by reference in their entirety.

FIELD

This present disclosure relates to herbicidal compositions and methods.

BACKGROUND

N-(2E,4E-Decadienoyl) pyrrolidine (also called sarmentine) was originally separated from the fruit of *Piper sarmentosum* in 1987 (Likhitwitayawuid, K. et al., *Tetrahedron* 1987 (43) 3689-3694) and also from *Piper nigrum* in 1988 (Kiuchi, F. et al., *Chemical and Pharmaceutical Bulletin* 1988(36):2452), and first synthesized in 1995 (Bernabeu, M. et al., *Tetrahedron Letters*, 1995 (36)3901-3904). Sarmentine has been found to exert the following activities: antioxidant activity in vivo, protecting photoaged skin (Cornacchione, S. et al., *J. Drugs in Dermatol.* 2007, 6S, 8-13); antiplatelet aggregation activity (Li, C. Y. et al., *J. Agric. Food Chem.* 2007, 55, 9436-9442); antiplasmodial and antimycobacterial activities (Tuntiwachwuttikul, P. et al., *Chem. Pharm. Bull.* 2006, 54, 149-151); and antituberculosis activity (Rukachaisirikul, T. et al., *J. Ethnopharmacol.*, 2004, 93, 173-176). Sarmentine has also been used as a solubilizer of hydrophobic compounds in cosmetics and pharmaceuticals (Stephen, T. et al., PCT Publication No. WO/2008/065451).

SUMMARY

Disclosed herein are methods for modulating (e.g., inhibiting) emergence and growth of monocotyledonous or dicotyledonous plants (e.g., weeds and grasses) using sarmentine and/or a sarmentine analogue and a second herbicide. The application of sarmentine and/or a sarmentine analogue and a second herbicide to the plant or its growth substrate results in synergistic pre- and/or post-emergence herbicidal activity against the plant. The present disclosure also provides compositions comprising sarmentine and/or a sarmentine analogue, in combination with a second herbicide. The present disclosure further provides uses of combinations of sarmentine and/or a sarmentine analogue with a second herbicide for the formulation and/or manufacture of herbicidal compositions for weed control, e.g., by application to weeds or its substrate.

In certain embodiments, the sarmentine or sarmentine analogue has the following structure:

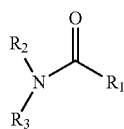

in which R1 is an alkyl, alkenyl, alkynyl, heterocyclyl, aromatic, aryl, NH-substituted, or N,N-substituted group, and the length of R1 is from 4 to 20 atoms, preferably from 6 to 12 atoms; R2 and R3 are alkyl, alkenyl, alkynyl, cycloalkyl, cycloalkenyl, aromatic, arylalkyl, heterocyclyl or heteroaryl groups, or R2+R3+N is an N-containing heterocyclic or herteroaryl ring consisting of between 3-18 atoms, preferably between 5 to 8 atoms.

In more particular embodiments, the sarmentine or sarmentine analogue includes but is not limited to (2E,4Z-Decadienoyl)pyrrolidine; (2E,4Z-Decadienoyl)hexamethleneimine; and N-(Decenoyl)hexamethyleneimine.

In a particular embodiment, the sarmentine has the following structure:

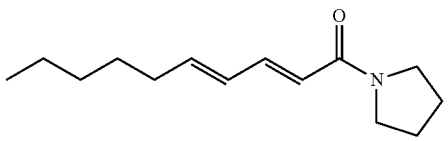 [SMILES: CCCCC/C=C/C=C/C(=O)N1CCCC1]

In certain embodiments, the compositions as disclosed herein contain between about 0.005 mg/ml to about 100 mg/ml of sarmentine and/or a sarmentine analogue; or between about 0.01 mg/ml to about 15 mg/ml of sarmentine and/or a sarmentine analogue; or between about 0.1 mg/ml to about 10 mg/ml of sarmentine and/or a sarmentine analogue. In additional embodiments, the compositions contain between about 10 mg/ml to about 25 mg/ml of sarmentine and/or a sarmentine analogue; or between about 10 mg/ml to about 35 mg/ml of sarmentine and/or a sarmentine analogue.

The second herbicidal agent can be any herbicide known in the art and can be used at any concentration sufficient for synergistic herbicidal activity with sarmentine and/or a sarmentine analogue. Exemplary herbicides include paclobutrazol and amicarbazone. In certain embodiments, the concentration of paclobutrazol is between about 0.04-1.4 mg/ml, or about 0.042-0.481 mg/ml, or about 0.047-0.293 mg/ml, or about 0.84-1.37 mg/ml. In additional embodiments, the concentration of amicarbazone is between about 0.25-2.8 mg/ml, or about 0.25-0.48 mg/ml, or about 0.315-1.228 mg/ml, or about 1.03-1.903 mg/ml, or about 0.31-0.544 mg/ml, or about 1.53-2.79 mg/ml.

The compositions can further comprise one or more phytopathogenic modulating agents (e.g., an anti-phytopathogenic agent) such as, for example, insecticides, fungicides, nematicides, viricides and/or bactericides. In addition, the compositions disclosed herein can comprise one or more carriers, surfactants, diluents, or stabilizers.

Additionally disclosed herein are methods for modulating emergence or growth of monocotyledonous or dicotyledonous weeds comprising applying to the weeds and/or a substrate an amount of sarmentine and/or a sarmentine analogue and a second herbicide effective to modulate emergence or growth of monocotyledonous or dicotyledonous weeds. The substrate can include but is not limited to soil, an artificial growth substrate (e.g., rice growing system), water or sediment. In one embodiment, sarmentine and/or a sarmentine analogue and a second herbicide may be applied to the substrate prior to emergence of said weed. Alternatively, sarmentine and/or a sarmentine analogue and a second herbicide may be applied to the substrate and/or weed after emergence of said weed(s). Sarmentine and/or a sarmentine analogue and the second herbicide may be applied together or separately. For example, sarmentine and/or a sarmentine analogue may be applied first followed by the second herbicide, or vice versa.

The weeds may be broadleaved and/or grass weeds. In certain embodiments, the weeds are members of the genuses *Poa* (e.g., Annual Bluegrass (*Poa annua*), Kentucky Bluegrass (*Poa pratensis*)); *Agrostis* (e.g., Creeping Bentgrass (*agrostis stolonifera*)); *Lolium* (e.g., Perennial Rye Grass (*Lolium perenne*)) or *Festuca* (e.g., Tall Fescue (*Festuca arundinacea*)).

DETAILED DESCRIPTION

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As used herein, the term "modulate" means to alter the rate of a process such as, for example, weed growth. Modulation can include either an increase or a decrease in rate. In certain embodiments, modulation of weed growth results in decreased growth, or even death, of the weed.

The terms "synergy," "synergism," "synergistic" and "synergistically" refer to a process in which two or more components having similar or the same activity (e.g., phytotoxic, herbicidal), when used together, have an effect that is greater than the sum of the individual activities. Thus, for example, a synergistic herbicidal effect results when a combination of two herbicides produces a greater effect than would be expected if the two herbicides acted independently.

An "analogue," for the purposes of the present disclosure, refers to a compound that is structurally similar to a reference compound. Analogues can be synthesized, for example, by using a backbone of a reference compound as starting material and adding, either randomly or in a prescribed fashion, additional functional groups. Alternatively, the reference compound itself can be chemically modified, either randomly or in prescribed fashion, to generate one or more analogues. An analogue can also be purified or isolated from natural sources. An analogue can have greater, the same, or lesser functional activity as compared to the reference compound from which it is derived.

As used herein, "substrate" refers to a surface or medium in which a plant grows. Substrate includes, but is not limited to, soil, an artificial growth surface or medium, water, and sediment.

Sarmentine and its Analogues

The sarmentine and/or its analogues used in the methods and compositions of the present invention may have the following structure:

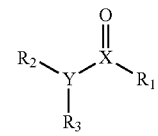

in which X includes but is not limited to sulfur, phosphorus, boron or carbon; Y includes but is not limited to carbon, oxygen, nitrogen, sulfur, boron or phosphorous; $R_1$ includes but is not limited to hydrogen, hydroxyl, halogen, alkyl, alkoxy, alkenyl, alkynyl, cycloalkyl, cycloalkenyl, aromatic, arylalkyl, heterocyclyl and heteroaryl; $R_2$ includes but is not limited to hydrogen, hydroxyl, halogen, alkyl, alkoxy, alkenyl, alkynyl, cycloalkyl, aromatic, arylalkyl, heterocyclyl and heteroaryl; $R_3$ includes but is not limited to hydrogen, hydroxyl, halogen, alkyl, alkoxy, alkenyl, alkynyl, cycloalkyl, aromatic, arylalkyl, heterocyclyl and heteroaryl; or wherein $R_2+R_3+Y$ can be a cyclic or heterocyclyl ring containing 4-50 atoms. Each of these is optionally substituted.

As used herein, the term "alkyl" refers to a saturated hydrocarbon radical which may be straight-chain or branched-chain (e.g., ethyl, isopropyl, t-amyl, or 2,5-dimethylhexyl, etc.). This definition applies both when the term is used alone and when it is used as part of a compound term.

The terms "cycloalkyl" and "cycloalkenyl" refer to a saturated hydrocarbon ring and includes bicyclic and polycyclic rings. Similarly, cycloalkyl and cycloalkenyl groups having a heteroatom (e.g., N, O, or S) in place of a carbon ring atom may be referred to as "heterocycloalkyl" or "heterocyclyl," and "heterocycloalkylene," respectively.

The term "alkenyl" as used herein refers to an alkyl group as described above which contains one or more sites of unsaturation that is a double bond. Similarly, the term "alkynyl" as used herein refers to an alkyl group as described above which contains one or more sites of unsaturation that is a triple bond.

The term "alkoxy" refers to an alkyl radical as described above which also bears an oxygen substituent which is capable of covalent attachment to another hydrocarbon radical (such as, for example, methoxy, ethoxy, aryloxy, and t-butoxy).

The term "aryl" refers to an aromatic carbocyclic substituent which may be a single ring or multiple rings which are fused together, linked covalently or linked to a common group such as an ethylene or methylene moiety. Aryl groups having a heteroatom (e.g., N, O, or S) in place of a carbon ring atom are referred to as "heteroaryl."

The terms "arylalkyl," "arylalkenyl," and "aryloxyalkyl" refer to an aryl radical attached directly to an alkyl group, an alkenyl group, or an oxygen atom which is attached to an alkyl group, respectively. For brevity, aryl as part of a combined term as above is meant to include heteroaryl as well.

The term "halo" or "halogen," by itself or as part of another substituent, means, unless otherwise stated, a fluorine, chlorine, bromine, or iodine atom. Additionally, terms such as "haloalkyl" are meant to include monohaloalkyl and polyhaloalkyl.

The term "hetero" as used in a "heteroatom-containing alkyl group" (i.e., a "heteroalkyl" group) or a "heteroatom-containing aryl group" (i.e., a "heteroaryl" group) refers to a molecule, linkage, or substituent in which one or more carbon atoms are replaced with an atom other than carbon, e.g., nitrogen, oxygen, sulfur, phosphorus, or silicon.

In certain embodiments, the sarmentine analogue has the following structure:

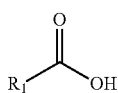

wherein $R_1$ is an alkyl, alkenyl, alkynyl, herterocyclyl, aromatic, aryl group, NH-substituted, or N,N-substituted group. In certain embodiments, $R_1$ is an alkyl or alkenyl moiety containing from 4 to 20 atoms and preferably from 6 to 12 atoms. In more specific embodiments, $R_1$ is a $C_{5-15}$ alkyl or $C_{5-15}$ alkenyl group. In yet more specific embodiments, $R_1$ is a $C_{6-12}$ alkyl or $C_{6-12}$ alkenyl group. Possible alkenyl moieties include but are not limited to linear alkenyl fatty acids, branched alkenyl fatty acids, cycloalkenyl substituted fatty acids (e.g., cyclohexenylpropanoic acid, cyclohexenylbutanoic acid, cyclohexenylpentanoic acid and so on), and heterocycloalkenyl (e.g., 4-[1,2,3,4-tetrahydropyridinyl] butanoic acid).

In additional embodiments, the sarmentine analogue has the following structure:

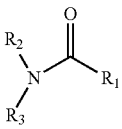

wherein $R_1$ is an alkyl, alkenyl, alkynyl, herterocyclyl, aromatic, aryl group, NH-substituted, or N,N-substituted group, the length of $R_1$ chain can be from 4 to 20 atoms, the preferred length will be from 6 to 12 atoms; wherein $R_2$ and $R_3$ are alkyl, alkenyl, alkynyl, cycloalkyl, cycloalkenyl, aromatic, arylalkyl, heterocyclyl or heteroaryl; or alternatively $R_2+R_3+N$ can be an N-containing heterocyclic or herteroaryl ring consisting of between 3-18 atoms and preferably between 5 to 8 atoms.

In certain embodiments, a sarmentine analogue has substantially the same activity as sarmentine. As defined herein "substantially the same activity as sarmentine" means at least about 80% of the herbicidal activity of sarmentine and preferably at least about 90% of the herbicidal activity of sarmentine and even more preferably at least about 95% of the herbicidal activity of sarmentine and still more preferably at least 99% of the herbicidal activity of sarmentine. The sarmentine analogue can also have better activity than sarmentine. For example, the sarmentine analogue may have at least about 105% of the herbicidal activity of sarmentine, 110% of the herbicidal activity of sarmentine, and 120%, 130%, 140%, 150%, and so forth, of the herbicidal activity of sarmentine.

One of skill in the art will appreciate that materials for weed or phytopathogen management as disclosed herein can include not only sarmentine, but any sarmentine analogue. Sarmentine analogues in these materials can be natural and/or synthesized.

In certain embodiments, sarmentine analogues are obtained from plants, fungi, bacteria and soils. In particular embodiments, sarmentine and its analogues used in the methods and compositions disclosed herein are obtained from the fruits, leaves, stems and roots of any *Piper* species. In more particular embodiments, non-limiting examples of *Piper* species that can contain sarmentine and/or sarmentine analogues include but are not limited to the following species, such as *Piper aborescens, P. acutisleginum, P. aduncum, P. amalago, P. argyrophylum, P. attenuatum, P. augustum, P. auranticaum, P. auritum, P. austrosinense* T., *P. arboricola* C. DC., *P. banksii, P. bartlingianum, P. betle* L., *P. boehmeriifolium* var. *tonkinense* C. DC., *P. brachystachyum, P. callosum, P. chaba, P. chiadoense, P. cubeba* L., *P. damiaoshaneense, P. demeraranum, P. falconeri, P. futokadsura, P. guayranum, P. guineense, P. hainanense* Hemsl. in F. B. Forbes and Hemsl., *P. hamiltonii, P. hancei* Maxim., *P. khasiana, P. kadsura* (Choisy) Ohwi, *P. laetispicum* C. DC., *P. longum* L., *P. longum* var. ("round peepal"), *P. macropodum, P. manii, P. marginatum P. martinii* C. DC., *P. methysticum, P. nepalense, P. novae hollandiae, P. nigrum* L., *P. nudibaccatum* Y. C. Tseng, *P. officinarum, P. peepuloides, P. pedicellosum, P. ponesheense* C. DC., *P. puberulilimbum* C. DC., *P. puberulum* (Benth.) Maxim., *P. pubicatulum* C. DC., *P. ridleyi, P. rugosum, P. retrofractum* Vahl, *P. ribesioides, P. sanctum, P. sarmentosum* R., *P. schmidtii, P. semiimmersum* C. DC., *P. sintenense, P. spirei* C. DC., *P. syvaticum, P. thomsoni, P. verruscosum, P. trichostachyon, P. wallichii* (Miq.), *P. wightii*. See, for example, Parma, V. et al., *Phytochem.* 1998 (49) 1069-1078. Sarmentine can also be found in grape (*Vitis* sp.) seeds.

Sarmentine analogues can also be obtained from microorganisms such as *Actinomycetes*. See, for example, Cho, J. et al., *J. Nat. Prod.*, 2007 (70) 1321-1328; and Askolar, R. et al., *J. Nat. Prod.*, 2006 (69), 1756-1759.

Sarmentine and sarmentine analogues can be extracted and purified by any physical and/or chemical means, e.g., from *Piper longum*, using procedures set forth in U.S. Pat. No. 8,466,192 (the disclosure of which is incorporated by reference herein for this purpose), or using procedures known in the art. See, for example, Likhitwitayawuid, K. et al., *Tetrahedron* 1987 (43) 3689-3694; and Kiuchi, F. et al., *Chemical and Pharmaceutical Bulletin* 1988(36):2452.

In a particular embodiment, a *Piper longum* sample is subjected to extraction with an alkyl alcohol, preferably methanol. The extract is then fractionated by, for example, column chromatography, more particularly by HPLC, and fractions containing sarmentine are identified by, for example bioassay.

Sarmentine and sarmentine analogues can also be chemically synthesized using, for example, the method set forth in Bernabeu, M. et al., *Tetrahedron Letter,* 1995 (36)3901.

In certain embodiments, the methods and compositions of the present invention use or contain the compound sarmentine, also known as N-(2E,4E-decadienoyl) pyrrolidine. Natural sarmentine can exist, e.g., in plant extracts or in a purified form.

Sarmentine analogues include, but are not limited to, N-(Decanoyl)pyrrolidine, N-(Decenoyl)pyrrolidine, N-(Decanoyl)piperidine, N-(trans-Cinnamoyl)pyrrolidine, (2E,4Z-Decadienoyl)pyrrolidine, N-(Decenoyl)piperidine, (2E,4Z-Decadienoyl)piperidine, (2E,4Z-Decadienoyl)hexamethyleneimine, N-(Decenoyl)hexamethyleneimine, N-(Decanoyl)hexamethyleneimine, Decanoic acid and 2E-Decenoic acid.

Formulations

Sarmentine and/or sarmentine analogue-containing herbicidal compositions (also alternatively referred to as "formulations") can be formulated in any form and by any method known in the art. Non-limiting examples of formulations include emulsifiable concentrates (EC), wettable powders (WP), soluble liquids (SL), aerosols, ultra-low volume concentrate solutions (ULV), soluble powders (SP), microencapsulations, water dispersed granules, flowables (FL), microemulsions (ME), nano-emulsions (NE), etc. In any formulation described herein, the percentage of sarmentine and/or its analogues is within a range of 0.01% to 99.99%. In a particular embodiment, a formulation may be free of surfactants.

The compositions disclosed herein can further comprise a carrier and/or diluent. The term, 'carrier' as used herein means an inert, organic or inorganic material, with which the active ingredient is mixed or formulated to facilitate its application to the soil, seed, plant or other object to be treated, or to facilitate its storage, transport and/or handling. Examples of carriers that can be used for application of a composition to a growth substrate include, but are not limited to, active charcoal, corn gluten meal, soybean meal, vermiculite, bentonite, kaolinite, wheat germ, almond hulls, cottonseed meal, Fuller's earth, orange pulp, rice hulls, sawdust, Gum arabic, etc. If desired, plant essential oils such as cinnamon, clove, thyme (eugenol as active ingredient), wintergreen, soy methyl ester, citronella, pine oil, citrus oil (1-limonene as active ingredient) and the like, can be included in the carrier. The active ingredient, either by itself or in the presence of a carrier, can be dissolved in, for example, an aqueous solution (e.g., water) or an organic solvent such as ethanol, formic acid or methanol.

Sarmentine and certain of its analogues can be oxidized because of the presence of two conjugated double bonds. This is exemplified by the fact that sarmentine can function as an in vivo antioxidant for photoaged skin. Cornacchione, S. et al., *J. Drugs in Dermatol.* 2007 (6 suppl) S8-13. Therefore, in certain embodiments, the compositions disclosed herein comprise an antioxidant to enhance herbicidal activity. Non-limiting examples of antioxidants include alpha-tocopherol, beta-carotene, ascorbic acid, zinc oxide, titanium oxide, *Gynostemma pentaphyllum* extract, *Vaccinium angustifolium* (Blueberry) fruit extract, *Pinus strobus* bark extract, rhaponticin, plankton extract, *Monostroma* sp. extract, algae extract, venuceane, and rosmarinic acid.

In certain embodiments, the herbicidal compositions disclosed herein additionally comprise one or more anti-phytopathogenic agents such as, for example, insecticides, fungicides, nematicides, viricides and/or bactericides. In these embodiments the compositions possess both herbicidal and anti-phytopathogenic activities, and can therefore be used in methods for controlling both weeds and plant pathogens.

Examples of phytopathogens that can be controlled using the compositions and methods disclosed herein include but are not limited to plant viruses, phytopathogenic fungi or bacteria, insects and nematodes. In certain embodiments, viruses include but are not limited to TMV, tobacco or cucumber mosaic virus, ringspot virus, necrosis virus, and maize dwarf mosaic virus. Phytopathogenic fungi include but are not limited to *Fusarium* sp., *Botrytis* sp., *Monilinia* sp., *Colletotrichum* sp, *Verticillium* sp.; *Microphomina* sp., *Phytophtora* sp., *Mucor* sp., *Rhizoctonia* sp., *Geotrichum* sp., *Phoma* sp., and *Penicillium* sp. Phytopathognic bacteria include but are not limited to *Bacillus* sp. and *Xanthomonas* sp.

Nematodes that can be controlled using the compositions and method of the present disclosure include but are not limited to parasitic nematodes such as root-knot, cyst, and lesion nematodes, including *Heterodera* and *Globodera* sp.; particularly *Globodera rostochiensis* and *G. pailida* (potato cyst nematodes); *Heterodera glycines* (soybean cyst nematode); *H. schachtii* (beet cyst nematode); and *H. avenae* (cereal cyst nematode).

Phytopathogenic insects controlled using the compositions and methods of the present disclosure include but are not limited to insects from the order (a) Lepidoptera, for example, *Acleris* sp., *Adoxophyes* sp., *Aegeria* sp., *Agrotis* sp., *Alabama argillaceae*, *Amylois* sp., *Anticarsia gemmatalis*, *Archips* sp., *Argyrotaenia* sp., *Autographa* sp., *Busseola fusca*, *Cadra cautella*, *Carposina nipponensis*, *Chilo* sp., *Choristoneura* sp., *Clysia ambiguella*, *Cnaphalocrocis* sp., *Cnephasia* sp., *Cochylis* sp., *Coleophora* sp., *Crocidolomia binotalis*, *Cryptophlebia leucotreta*, *Cydia* sp., *Diatraea* sp., *Diparopsis castanea*, *Earias* sp., *Ephestia* sp., *Eucosma* sp., *Eupoecilia ambiguella*, *Euproctis* sp., *Euxoa* sp., *Grapholita* sp., *Hedya nubiferana*, *Heliothis* sp., *Hellula undalis*, *Hyphantria cunea*, *Keiferia lycopersicella*, *Leucoptera scitella*, *Lithocollethis* sp., *Lobesia botrana*, *Lymantria* sp., *Lyonetia* sp., *Malacosoma* sp., *Mamestra brassicae*, *Manduca sexta*, *Operophtera* sp., *Ostrinia nubilalis*, *Pammene* sp., *Pandemis* sp., *Panolis flammea*, *Pectinophora gossypiella*, *Phthorimaea operculella*, *Pieris rapae*, *Pieris* sp., *Plutella xylostella*, *Prays* sp., *Scirpophaga* sp., *Sesamia* sp., *Sparganothis* sp, *Spodoptera* sp, *Synanthedon* sp., *Thaumetopoea* sp., *Tortrix* sp., *Trichoplusia ni* and *Yponomeuta* sp.; (b) Coleoptera, for example, *Agriotes* sp., *Anthonomus* sp., *Atomaria linearis*, *Chaetocnema tibialis*, *Cosmopolites* sp., *Curculio* sp., *Dermestes* sp., *Diabrotica* sp., *Epilachna* sp., *Eremnus* sp., *Leptinotarsa decemlineata*, *Lissorhoptrus* sp., *Melolontha* sp., *Orycaephilus* sp., *Otiorhynchus* sp., *Phlyctinus* sp., *Popillia* sp., *Psylliodes* sp., *Rhizopertha* sp., *Scarabeidae*, *Sitophilus* sp., *Sitotroga* sp., *Tenebrio* sp., *Tribolium* sp. and *Trogoderma* sp.; (c) Orthoptera, for example, *Blatta* sp., *Blattella* sp., *Gryllotalpa* sp., *Leucophaea maderae*, *Locusta* sp., *Periplaneta* sp. and *Schistocerca* sp.; (d) Isoptera, for example, *Reticulitermes* sp.; (e) Psocoptera, for example, *Liposcelis* sp.; (f) Anoplura, for example, *Haematopinus* sp., *Linognathus* sp., *Pediculus* sp., *Pemphigus* sp. and *Phylloxera* sp.; (g) Mallophaga, for example, *Damalinea* sp. and *Trichodectes* sp.; (h) Thysanoptera, for example, *Frankliniella* sp., *Hercinotnrips* sp., *Taeniothrips* sp., *Thrips palmi*, *Thrips tabaci* and *Scirtothrips aurantii*; (i) Heteroptera, for example, *Cimex* sp., *Distantiella theobroma*, *Dysdercus* sp., *Euchistus* sp., *Eurygaster* sp., *Leptocorisa* sp., *Nezara* sp., *Piesma* sp., *Rhodnius* sp., *Sahlbergella singularis*, *Scotinophara* sp. and *Tniatoma* sp.; (j) Homoptera, for example, *Aleurothrixus floccosus*, *Aleyrodes brassicae*, *Aonidiella* sp., *Aphididae*, *Aphis* sp., *Aspidiotus* sp., *Bemisia tabaci*, *Ceroplaster* sp., *Chrysomphalus aonidium*, *Chrysomphalus dictyospermi*, *Coccus hesperidum*, *Empoasca* sp., *Eriosoma larigerum*, *Erythroneura* sp., *Gascardia* sp., *Laodelphax* sp., *Lecanium corni*, *Lepidosaphes* sp., *Macrosiphus* sp., *Myzus* sp., *Nephotettix* sp., *Nilaparvata* sp., *Paratoria* sp., *Pemphigus* sp., *Planococcus* sp., *Pseudaulacaspis* sp., *Pseudococcus* sp., *Psylla* sp., *Pulvinaria aethiopica*, *Quadraspidiotus* sp., *Rhopalosiphum* sp., *Saissetia* sp., *Scaphoideus* sp., *Schizaphis* sp., *Sitobion* sp., *Trialeurodes vaporariorum*, *Trioza erytreae* and *Unaspis citri*; (k) Hymenoptera, for example, *Acromyrmex*, *Atta* sp., *Cephus* sp., *Diprion* sp., *Diprionidae*, *Gilpinia polytoma*, *Hoplocampa* sp., *Lasius* sp., *Monomorium pharaonis*, *Neodiprion* sp., *Solenopsis* sp. and *Vespa* sp.; (l) Diptera, for example, *Aedes* sp., *Antherigona soccata, Bibio hortulanus, Calliphora erythrocephala, Ceratitis* sp., *Chrysomyia* sp., *Culex* sp., *Cuterebra* sp., *Dacus* sp., *Drosophila melanogaster, Fannia* sp., *Gastrophilus* sp., *Glossina* sp., *Hypoderma* sp., *Hyppobosca* sp., *Liriomyza* sp., *Lucilia* sp., *Melanagromyza* sp., *Musca* sp., *Oestrus* sp., *Orseolia* sp., *Oscinella frit, Pegomyia hyoscyami, Phorbia* sp., *Rhagoletis pomonella, Sciara* sp., *Stomoxys* sp., *Tabanus* sp., *Tannia* sp. and *Tipula* sp.; (m) *Siphonaptera*, for example, *Ceratophyllus* sp. and *Xenopsylla cheopis* and (n) from the order Thysanura, for example, *Lepisma saccharina*.

The compositions and methods disclosed herein can further be used for controlling crucifer flea beetles (*Phyllotreta* sp.), root maggots (*Delia* sp.), cabbage seedpod weevil (*Ceutorhynchus* sp.) and aphids in oil seed crops such as canola (rape), mustard seed, and hybrids thereof, and also rice and maize.

The compositions disclosed herein can further comprise an additional fungicidal agent such as myclobutanil, fenhexamide, azoxystrobin, azoxystrobin combination, boscalid, *Bacillus subtilis*, copper sulfate, chlorothalonil, copper hydroxide, cymoxanil, dimethomorph, dechloropropene, fosetyl-aluminum, fludioxonil, fenamidone, iprodione, mefenoxam, mancozeb, metalaxyl, metam sodium, potassium bicarbonate, pyraclostrobin, propiconazole, propicocarb, thiram, thiabendazole, thiophanate-methyl, trifloxystrobin, vinclozolin, sulfur, and/or ziram. They can also include antibacterial agents such as, for example, streptomycin and oxytetracycline.

The percentage of sarmentine and/or a sarmentine analogue in any of these compositions can be within a range of 0.01% to 99.99%.

Non-limiting examples of natural herbicides that can be used with sarmentine and/or a sarmentine analogue include but are not limited to catechin, ellagic acid, sorgoleone, juglone, ceratiolin, leptospermone, thaxtomin, acetic acid, citric acid, iron chelate, *Phoma macrostoma*, bialophos, usnic acid, 1,8-cineole, geranial, neral, cinmethylin, solstitiolide, ailanthone, chaparrine, ailanthinol B, hydroxamic acids, glucohirsutin, hirsutin, arabin, and meta-tyrosine.

In other embodiments, non-limiting examples of synthetic herbicides that can be used with sarmentine and/or a sarmentine analogue include but are not limited to aryloxyphenoxypropionic herbicides (e.g., chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop); benzoic acid herbicides (e.g., chloramben, dicamba, 2,3,6-TBA and tricamba); benzofuranyl alkylsulfonate herbicides (e.g., benfuresate and ethofumesate); benzoylcyclohexanedione herbicides (e.g., mesotrione, sulcotrione, tefuryltrione and tembotrione); carbamate herbicides (e.g., asulam, carboxazole chlorprocarb, dichlormate, fenasulam, karbutilate and terbucarb); carbanilate herbicides (e.g., barban, BCPC, carbasulam, carbetamide, CEPC, chlorbufam, chlorpropham, CPPC, desmedipham, phenisopham, phenmedipham, phenmediphamethyl, propham); cyclohexene oxime herbicides (e.g., alloxydim, butroxydim, clethodim, cloproxydim, cycloxydim, profoxydim, sethoxydim, tepraloxydim and tralkoxydim); cyclopropylisoxazole herbicides (e.g., isoxachlortole and isoxaflutole); dicarboximide herbicides (e.g., benzfendizone, cinidon-ethyl, flumezin, flumiclorac, flumioxazin and flumipropyn); dinitroaniline herbicides (e.g., benfluralin, butralin, dinitramine, ethalfluralin, fluchloralin, isopropalin, methalpropalin, nitralin, oryzalin, pendimethalin, prodiamine, profluralin and trifluralin); dinitrophenol herbicides (e.g., dinofenate, dinoprop, dinosam, dinoseb, dinoterb, DNOC, etinofen and medinoterb); dithiocarbamate herbicides (e.g., dazomet and metam; halogenated aliphatic herbicides such as alorac, chloropon, dalapon, flupropanate, hexachloroacetone, iodomethane, methyl bromide, monochloroacetic acid, SMA and TCA); imidazolinone herbicides (e.g., imazamethabenz, imazamox, imazapic, imazapyr, imazaquin and imazethapyr); inorganic herbicides (e.g., ammonium sulfamate, borax, calcium chlorate, copper sulfate, ferrous sulfate, potassium azide, potassium cyanate, sodium azide, sodium chlorate and sulfuric acid); nitrophenyl ether herbicides (e.g., acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen); nitrile herbicides (e.g., bromobonil, bromoxynil, chloroxynil, dichlobenil, iodobonil, ioxynil and pyraclonil); organophosphorus herbicides (e.g., amiprofos-methyl, anilofos, bensulide, bilanafos, butamifos, 2,4-DEP, DMPA, EBEP, fosamine, glufosinate, glyphosate and piperophos); phenoxy herbicides (e.g., bromofenoxim, clomeprop, 2,4-DEB, 2,4-DEP, difenopenten, disul, erbon, etnipromid, fenteracol and trifopsime); phenoxyacetic herbicides (e.g., 4-CPA, 2,4-D, 3,4-DA, MCPA, MCPA-thioethyl and 2,4,5-T); phenoxybutyric herbicides (e.g., 4-CPB, 2,4-DB, 3,4-DB, MCPB and 2,4,5-TB); phenoxypropionic herbicides (e.g., cloprop, 4-CPP, dichlorprop, dichlorprop-P, 3,4-DP, fenoprop, mecoprop and mecoprop-P); phenylenediamine herbicides (e.g., dinitramine and prodiamine); picolinic acid herbicides (e.g., aminopyralid, clopyralid and picloram); pyrazolyl herbicides (e.g., benzofenap, pyrazolynate, pyrasulfotole, pyrazoxyfen, pyroxasulfone and topramezone); pyrazolylphenyl herbicides (e.g., fluazolate and pyraflufen; pyridazine herbicides such as credazine, pyridafol and pyridate); pyridazinone herbicides (e.g., brompyrazon, chloridazon, dimidazon, flufenpyr, metflurazon, norflurazon, oxapyrazon and pydanon); pyridine herbicides (e.g., cliodinate, dithiopyr, fluroxypyr, haloxydine, picolinafen, pyriclor, thiazopyr and triclopyr); pyrimidinediamine herbicides (e.g., iprymidam and tioclorim); quaternary ammonium herbicides (e.g., cyperquat, diethamquat, difenzoquat, diquat, morfamquat and paraquat); pyrimidinyloxybenzoic acid herbicides (e.g., bispyribac and pyriminobac); thiocarbamate herbicides (e.g., butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, triallate and vemolate); sulfonamide herbicides (e.g. asulam, carbasulam, fenasulam, oryzalin, penoxsulam, pyroxsulam); triazine herbicides (e.g., dipropetryn, triaziflam and trihydroxytriazine, atrazine, chlorazine, cyanazine, cyprazine, eglinazine, ipazine, mesoprazine, procyazine, proglinazine, propazine, sebuthylazine, simazine, terbuthylazine and trietazine, atraton, methometon, prometon, secbumeton, simeton and terbumeton; ametryn, aziprotryne, cyanatryn, desmetryn, dimethametryn, methoprotryne, prometryn, simetryn and terbutryn); triazinone herbicides (e.g., ametridione, amibuzin, hexazinone, isomethiozin, metamitron and metribuzin); triazolopyrimidine herbicides (e.g., chloransulam, diclosulam, florasulam, flumetsulam, metosulam); urea herbicides (e.g., benzthiazuron, cumyluron, cycluron, dichloralurea, diflufenzopyr, isonoruron, isouron, methabenzthiazuron, monisouron and noruron; anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron and thidiazuron; amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; chlorsulfuron, cinosulfuron, ethametsulfuron, iodosulfuron, metsulfuron, prosulfuron, thifensulfuron, triasulfuron, tribenuron, triflusulfuron and tritosulfuron; buthiuron, ethidimuron, tebuthiuron, thiazafluron and thidiazuron), etc.

In additional embodiments, the methods of the present invention comprise the use of the herbicide paclobutrazol and/or the herbicide amicarbazone, in addition to sarmentine and/or a sarmentine analogue. Paclobutrazol is a plant growth regulator herbicide that interrupts the gibberellic acid (GA) synthesis pathway, causing inhibition of cell elongation. Amicarbazone is a photosystem II inhibitor, belonging to the triazolinone class of herbicides.

In further embodiments, the compositions disclosed herein comprise the herbicide paclobutrazol and/or the herbicide amicarbazone in combination with sarmentine and/or a sarmentine analogue.

Sarmentine and/or a sarmentine analogue, when used with paclobutrazol or amicarbazone, exerts synergistic herbicidal activity compared to sarmentine and/or a sarmentine analogue alone, or paclobutrazol alone, or amicarbazone alone, against a number of weeds and grasses, including annual bluegrass (*Poa annua*), Kentucky bluegrass (*Poa pratensis*), perennial ryegrass (*Lolium perenne*), tall fescue (*Festuca arundinacea*) and creeping bentgrass (*Agrostis stolonifera*). See Examples 1 and 2 infra.

The composition and method of the present disclosure will be further illustrated in the following non-limiting examples. The examples are illustrative of various embodiments only and do not limit the claimed invention regarding the materials, conditions, weight ratios, process parameters and the like recited herein.

EXAMPLES

Methods for the isolation and purification of sarmentine; methods for the synthesis of sarmentine analogues, the structures and properties of sarmentine analogues; data on structure-activity relationships of various sarmentine analogues; bioassays; and methods for evaluation of herbicidal activity of sarmentine and sarmentine analogues are provided in U.S. Pat. No. 8,466,192, the disclosure of which in incorporated by reference in its entirety for the purposes of describing the aforementioned methods, structures, properties, bioassays and data.

Example 1

Synergistic Activity of Sarmentine and Paclobutrazol on Grasses

Post-emergent effects of sarmentine and paclobutrazol were evaluated on annual bluegrass (*Poa annua*), Kentucky bluegrass (*Poa pratensis*), and Creeping Bentgrass (*Agrostis stolonifera*).

*P. annua* is among the most common weeds in golf courses, park lawns and other turf areas; the other species tested represent a range of common turf grass species. Paclobutrazol is a plant growth regulator herbicide that interrupts the gibberellic acid (GA) synthesis pathway causing inhibition of cell elongation. Sarmentine is a contact herbicide with a broad spectrum of activity on both grasses and broadleaves. See, for example, U.S. Pat. No. 8,466,192.

For each of the three species tested, fifteen seedlings at the 1-2 leaf stage, in 2.5 cm square pots containing plant growth mix, were sprayed with two suboptimal doses of sarmentine, two suboptimal doses of paclobutrazol, or a factorial combination thereof, as shown in Tables 1-3. A volume of 40 gal/Acre was applied, using a cabinet track sprayer. Negative controls were sprayed with water. Pots were randomly placed in a growth room at 25° C. and 50% relative humidity, and watered as necessary. Treatments were arranged in a 2 k factorial design with three repeat measures and evaluated for fresh weight at 14 days after application. Potential synergy was evaluated by calculating the ratio of observed (E) to expected (Ee) percent of control weight, according to Colby's formula. Colby (1967) *Weeds* 15:20-22. Percent control was calculated in relation to the untreated control (0% control) with 100% control denoting no living green tissue remaining at 14 days after treatment. An E/Ee score above 1.0 indicates a synergistic interaction between two substances.

TABLE 1

Treatment of *Poa annua* with sarmentine and paclobutrazol

| Sample number | Sarmentine (mg/ml) | Paclobutrazol (mg/ml) | AVG Fresh Weight (g) | SE (g) | % Control | Ee (Expected Control) | E/Ee |
|---|---|---|---|---|---|---|---|
| 1 | 12.47 | 0.84 | 0.46 | 0.03 | 22.9 | 20.8 | 1.1 |
| 2 | 17.114 | 0.84 | 0.35 | 0.07 | 42.1 | 28.8 | 1.5 |
| 3 | 12.47 | 1.37 | 0.43 | 0.04 | 28.3 | 7.9 | 3.6 |
| 4 | 17.114 | 1.37 | 0.42 | 0.07 | 30.0 | 17.1 | 1.8 |
| 5 | 12.47 | 0 | 0.71 | 0.05 | 0.0 | — | — |
| 6 | 17.114 | 0 | 0.54 | 0.03 | 10.0 | — | — |
| 7 | 0 | 0.84 | 0.48 | 0.03 | 20.8 | — | — |
| 8 | 0 | 1.37 | 0.55 | 0.01 | 7.9 | — | — |
| 9 | 0 | 0 | 0.60 | 0.04 | 0.0 | — | — |

TABLE 2

Treatment of *Poa pratensis* with sarmentine and paclobutrazol

| Sample Number | Sarmentine (mg/ml) | Paclobutrazol (mg/ml) | AVG Fresh Weight (g) | SE (g) | % Control | Ee (Expected Control) | E/Ee |
|---|---|---|---|---|---|---|---|
| 1 | 19.15 | 0.0467 | 0.5 | 0.0 | 30.2 | 23.9 | 1.3 |
| 2 | 23.553 | 0.0467 | 0.5 | 0.1 | 30.7 | 20.6 | 1.5 |
| 3 | 19.15 | 0.293 | 0.5 | 0.1 | 33.0 | 7.5 | 4.4 |
| 4 | 23.553 | 0.293 | 0.6 | 0.0 | 22.2 | 7.5 | 2.9 |
| 5 | 19.15 | 0 | 0.6 | 0.1 | 11.3 | — | — |
| 6 | 23.553 | 0 | 0.7 | 0.0 | 7.5 | — | — |
| 7 | 0 | 0.0467 | 0.6 | 0.1 | 14.2 | — | — |
| 8 | 0 | 0.293 | 0.7 | 0.1 | 0.0 | — | — |
| 9 | 0 | 0 | 0.7 | 0.1 | 0.0 | — | — |

TABLE 3

Treatment of *Agrostis stolonifera* with sarmentine and paclobutrazol

| Sample Number | Sarmentine (mg/ml) | Paclobutrazol (mg/ml) | AVG Fresh Weight (g) | SE (g) | % Control | Ee (Expected Control) | E/Ee |
|---|---|---|---|---|---|---|---|
| 1 | 17.43 | 0.042 | 0.59 | 0.02 | 12.0 | 6.4 | 1.9 |
| 2 | 24.72 | 0.042 | 0.48 | 0.01 | 28.8 | 20.6 | 1.4 |
| 3 | 17.43 | 0.481 | 0.64 | 0.09 | 4.9 | 8.5 | 0.6 |
| 4 | 24.72 | 0.481 | 0.52 | 0.01 | 22.9 | 22.4 | 1.0 |
| 5 | 17.43 | 0 | 0.63 | 0.03 | 6.4 | — | — |
| 6 | 24.72 | 0 | 0.53 | 0.04 | 20.6 | — | — |
| 7 | 0 | 0.042 | 0.76 | 0.07 | 0.0 | — | — |
| 8 | 0 | 0.481 | 0.65 | 0.06 | 2.3 | — | — |
| 9 | 0 | 0 | 0.67 | 0.05 | 0.0 | — | — |

The results are shown in Tables 1-3.

Table 1 shows that sarmentine and paclobutrazol have an average E/Ee value of 2.0 when applied to *Poa annua*, which is indicative of a synergistic herbicidal effect on *P. annua*. Greater control was achieved with the lower concentration of paclobutrazol.

Table 2 shows that sarmentine and paclobutrazol have an average E/Ee value of 2.525 when applied to *Poa pratensis*, which is indicative of a synergistic herbicidal effect on *P. pratensis*.

Table 3 shows that sarmentine and paclobutrazol have an average E/Ee value of 1.225 when applied to *Agrostis stolonifera*, which is indicative of a slightly synergistic herbicidal effect on *A. stolonifera*. Synergy is at its highest with low concentrations of paclobutrazol and high concentrations of sarmentine.

Example 2

Synergistic Activity of Sarmentine and Amicarbazone on Grasses

Post-emergent effects of sarmentine and amicarbazone were evaluated on annual bluegrass (*Poa annua*), Kentucky bluegrass (*Poa pratensis*), Perennial ryegrass (*Lolium perenne*), Tall fescue (*Festuca arundinacea*) and Creeping Bentgrass (*Agrostis stolonifera*).

*P. annua* is among the most common weeds in golf courses, park lawns and other turf areas; the other four species tested represent a range of common turf grass species. Amicarbazone is a photosystem II inhibitor, belonging to the triazolinone class of herbicides. As discussed above, sarmentine is a contact herbicide with a broad spectrum of activity on both grasses and broadleaves.

For each of the five species tested, fifteen seedlings at the 1-2 leaf stage, in 2.5 cm square pots containing plant growth mix, were sprayed with two suboptimal doses of sarmentine, two suboptimal doses of amicarbazone, or a factorial combination thereof, as shown in Tables 4-8. A volume of 40 gal/Acre was applied, using a cabinet track sprayer. Negative controls were sprayed with water. Pots were randomly placed in a growth room at 25° C. and 50% relative humidity, and watered as necessary. Treatments were arranged in a 2 k factorial design with three repeat measures and evaluated for fresh weight at 14 days after application. Potential synergy was evaluated by calculating the ratio of observed (E) to expected (Ee) percent of control weight, according to Colby's formula. Colby (1967) *Weeds* 15:20-22. Percent control was calculated in relation to the untreated control (0% control) with 100% control denoting no living green tissue remaining at 14 days after treatment. An E/Ee score above 1.0 indicates a synergistic interaction between two substances.

TABLE 4

Treatment of *Poa annua* with sarmentine and amicarbazone

| Sample Number | Sarmentine (mg/ml) | Amicarbazone (mg/ml) | Avg Fresh Weight (g) | SE (g) | % Control | Ee (Expected Control) | E/Ee |
|---|---|---|---|---|---|---|---|
| 1 | 12.47 | 1.53 | 0.17 | 0.02 | 82.5 | 45.7 | 1.8 |
| 2 | 17.11 | 1.53 | 0.21 | 0.01 | 77.8 | 53.4 | 1.5 |

TABLE 4-continued

Treatment of *Poa annua* with sarmentine and amicarbazone

| Sample Number | Sarmentine (mg/ml) | Amicarbazone (mg/ml) | Avg Fresh Weight (g) | SE (g) | % Control | Ee (Expected Control) | E/Ee |
|---|---|---|---|---|---|---|---|
| 3 | 12.47 | 2.79 | 0.14 | 0.04 | 84.9 | 51.6 | 1.6 |
| 4 | 17.11 | 2.79 | 0.21 | 0.01 | 77.8 | 58.5 | 1.3 |
| 5 | 12.47 | 0 | 0.85 | 0.06 | 10.3 | — | — |
| 6 | 17.11 | 0 | 0.73 | 0.06 | 23.0 | — | — |
| 7 | 0 | 1.53 | 0.57 | 0.07 | 39.4 | — | — |
| 8 | 0 | 2.79 | 0.51 | 0.06 | 46.0 | — | — |
| 9 | 0 | 0 | 0.95 | 0.09 | 0.0 | — | — |

TABLE 5

Treatment of *Poa pratensis* with sarmentine and amicarbazone

| Sample Number | Sarmentine (mg/ml) | Amicarbazone (mg/ml) | AVG Fresh Weight (g) | SE (g) | % Control | Ee (Expected Control) | E/Ee |
|---|---|---|---|---|---|---|---|
| 1 | 19.15 | 0.31 | 0.40 | 0.04 | 49.6 | 9.6 | 5.2 |
| 2 | 23.553 | 0.31 | 0.47 | 0.06 | 41.2 | 9.9 | 4.2 |
| 3 | 19.15 | 0.544 | 0.36 | 0.03 | 54.3 | 35.9 | 1.5 |
| 4 | 23.553 | 0.544 | 0.37 | 0.06 | 53.4 | 36.1 | 1.5 |
| 5 | 19.15 | 0 | 0.72 | 0.08 | 9.6 | — | — |
| 6 | 23.553 | 0 | 0.72 | 0.04 | 9.9 | — | — |
| 7 | 0 | 0.31 | 0.84 | 0.01 | 0.0 | — | — |
| 8 | 0 | 0.544 | 0.56 | 0.03 | 29.1 | — | — |
| 9 | 0 | 0 | 0.79 | 0.00 | 0.0 | — | — |

TABLE 6

Treatment of *Lolium perenne* with sarmentine and amicarbazone

| Sample Number | Sarmentine (mg/ml) | Amicarbazone (mg/ml) | AVG Fresh Weight (g) | SE (g) | % Control | Ee (Expected Control) | E/Ee |
|---|---|---|---|---|---|---|---|
| 1 | 10 | 1.03 | 0.78 | 0.07 | 43.7 | 43.1 | 1.0 |
| 2 | 20 | 1.03 | 0.61 | 0.11 | 56.1 | 38.2 | 1.5 |
| 3 | 10 | 1.903 | 0.37 | 0.03 | 73.3 | 47.1 | 1.6 |
| 4 | 20 | 1.903 | 0.33 | 0.02 | 76.2 | 42.6 | 1.8 |
| 5 | 10 | 0 | 1.14 | 0.05 | 17.7 | — | — |
| 6 | 20 | 0 | 1.24 | 0.08 | 10.6 | — | — |
| 7 | 0 | 1.03 | 0.96 | 0.09 | 30.9 | — | — |
| 8 | 0 | 1.903 | 0.89 | 0.12 | 35.7 | — | — |
| 9 | 0 | 0 | 1.39 | 0.19 | 0.0 | — | — |

TABLE 7

Treatment of *Festuca arundinacea* with sarmentine and amicarbazone

| Sample number | Sarmentine (mg/ml) | Amicarbazone (mg/ml) | AVG Fresh Weight (g) | SE (g) | % Control | Ee (Expected Control) | E/Ee |
|---|---|---|---|---|---|---|---|
| 1 | 10.27 | 0.315 | 1.9 | 0.1 | 24.6 | 34.1 | 0.7 |
| 2 | 33.98 | 0.315 | 2.0 | 0.2 | 20.5 | 45.2 | 0.5 |
| 3 | 10.27 | 1.228 | 1.3 | 0.1 | 48.4 | 35.7 | 1.4 |
| 4 | 33.98 | 1.228 | 1.2 | 0.1 | 50.6 | 46.4 | 1.1 |
| 5 | 10.27 | 0 | 1.8 | 0.2 | 28.4 | — | — |
| 6 | 33.98 | 0 | 1.5 | 0.1 | 40.4 | — | — |
| 7 | 0 | 0.315 | 2.3 | 0.1 | 8.1 | — | — |
| 8 | 0 | 1.228 | 2.2 | 0.6 | 10.2 | — | — |
| 9 | 0 | 0 | 2.5 | 0.3 | 0.0 | — | — |

TABLE 8

Treatment of *Agrostis stolonifera* with sarmentine and amicarbazone

| Sample Number | Sarmentine (mg/ml) | Amicarbazone (mg/ml) | AVG Fresh Weight (g) | SE (g) | % Control | Ee (Expected Control) | E/Ee |
|---|---|---|---|---|---|---|---|
| 1 | 17.43 | 0.251 | 0.24 | 0.03 | 65.4 | 19.6 | 3.3 |
| 2 | 24.72 | 0.251 | 0.24 | 0.02 | 65.4 | 44.3 | 1.5 |
| 3 | 17.43 | 0.481 | 0.18 | 0.01 | 74.0 | 29.7 | 2.5 |
| 4 | 24.72 | 0.481 | 0.20 | 0.01 | 71.2 | 51.3 | 1.4 |
| 5 | 17.43 | 0 | 0.59 | 0.06 | 0.0 | — | — |
| 6 | 24.72 | 0 | 0.48 | 0.04 | 30.8 | — | — |
| 7 | 0 | 0.251 | 0.56 | 0.04 | 19.6 | — | — |
| 8 | 0 | 0.481 | 0.49 | 0.05 | 29.7 | — | — |
| 9 | 0 | 0 | 0.69 | 0.04 | 0.0 | — | — |

The results are shown in Tables 4-8.

Table 4 shows that sarmentine and amicarbazone have an average E/Ee value of 1.55 when applied to *Poa annua*, which is indicative of a synergistic herbicidal effect on *P. annua*.

Table 5 shows that sarmentine and amicarbazone have an average E/Ee value of 3.1 when applied to *Poa pratensis*, which is indicative of a synergistic herbicidal effect on *P. pratensis*.

Table 6 shows that sarmentine and amicarbazone have an average E/Ee value of 1.475 when applied to *Lolium perenne*, which is indicative of a mildly synergistic herbicidal effect on *L. perenne* at these concentrations. At higher concentrations of sarmentine and amicarbazone, greater control is achieved.

Table 7 shows that, when sarmentine and amicarbazone are applied to *Festuca arundinacea*, E/Ee values range from 0.5 to 1.4. Thus, at the higher concentrations of the two herbicides, a synergistic herbicidal effect on *F. arundinacea* is observed.

Table 8 shows that sarmentine and amicarbazone have an average E/Ee value of 2.175 when applied to *Agrostis stolonifera*, which is indicative of a synergistic herbicidal effect on *A. stolonifera*.

Although the preceding subject matter has been described with reference to specific embodiments, the details thereof are not to be construed as limiting, as one of skill in the art can use various equivalents, changes and modifications and still be within the scope of the present disclosure.

Various references are cited throughout this specification, each of which is incorporated herein by reference in its entirety.

What is claimed is:

1. A method for modulating emergence of annual bluegrass (*Poa annua*), Kentucky bluegrass (*Poa pratensis*), perennial ryegrass (*Lolium perenne*), tall fescue (*Festuca arundinacea*) or creeping bentgrass (*Agrostis stolonifera*), comprising contacting the plant or its growth substrate with:
   (a) sarmentine and
   (b) amicarbazone;
   wherein said sarmentine and amicarbazone have a synergistic herbicidal effect on the plant, and
   wherein the concentration of said sarmentine is between 10 and 34 mg/ml and the concentration of said amicarbazone is between 0.04 and 2.8 mg/ml.

2. A synergistic herbicidal composition comprising sarmentine and amicarbazone, wherein the concentration of sarmentine is between 10 and 34 mg/ml, and the concentration of said amicarbazone is between 0.04 and 2.8 mg/ml, and wherein the herbicidal composition modulates the emergence of annual bluegrass (*Poa annua*), Kentucky bluegrass (*Poa pratensis*), perennial ryegrass (*Lolium perenne*), tall fescue (*Festuca arundinacea*) or creeping bentgrass (*Agrostis stolonifera*).

3. The composition of claim 1, further comprising one or more of a carrier, a surfactant or a diluent.

* * * * *